(12) United States Patent
Kume et al.

(10) Patent No.: US 8,967,002 B2
(45) Date of Patent: Mar. 3, 2015

(54) GAS SENSOR AND GAS SENSOR INSTALLATION STRUCTURE

(75) Inventors: Makoto Kume, Inuyama (JP); Nobuhiro Inoue, Tajimi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 521 days.

(21) Appl. No.: 13/442,741

(22) Filed: Apr. 9, 2012

(65) Prior Publication Data
US 2012/0255356 A1    Oct. 11, 2012

(30) Foreign Application Priority Data

Apr. 8, 2011 (JP) ................. 2011-086610
Feb. 27, 2012 (JP) ................. 2012-040226

(51) Int. Cl.
*G01D 21/00*     (2006.01)
*G01N 27/407*    (2006.01)
*F01N 13/00*     (2010.01)
*F01N 13/18*     (2010.01)

(52) U.S. Cl.
CPC .......... *G01N 27/4078* (2013.01); *F01N 13/008* (2013.01); *F01N 13/1855* (2013.01)
USPC ....................................... 73/866.5

(58) Field of Classification Search
None
See application file for complete search history.

(56) References Cited

U.S. PATENT DOCUMENTS 5,707,152 A * 1/1998 Krywitsky ............. 374/208
6,796,175 B2   9/2004 Kurachi et al.
6,857,316 B2   2/2005 Kurachi et al.
7,434,448 B2  10/2008 Weyl et al.
2002/0148279 A1 10/2002 Weyl et al.

FOREIGN PATENT DOCUMENTS

| JP | 1-131156 U | 9/1989 |
| JP | 2001-221769 A | 8/2001 |
| JP | 2003-294685 A | 10/2003 |
| JP | 2003-532892 A | 11/2003 |
| JP | 2006-514311 A | 4/2006 |

OTHER PUBLICATIONS

Japanese Office Action ("Notification of Reasons for Rejection") dated Nov. 5, 2013 for corresponding Japanese Patent Application No. 2012-040226.

* cited by examiner

*Primary Examiner* — Robert R Raevis
(74) *Attorney, Agent, or Firm* — Sughrue Mion, PLLC

(57) ABSTRACT

A sensor (200) includes a sensor element (10), a tubular metallic shell (138), and a tubular mounting member (180) rotatable relative to the metallic shell. The metallic shell has a body (138*a*) and a flange (138*f*) provided forward of the mounting member and projecting radially outward beyond the radially inner surface of the mounting member. Further, the radially outer surface of the body and the rearward-oriented surface of the flange are connected by a slant surface (138*t*). The mounting member is such that a forward-oriented surface (180*a*) and a radially inner surface (180*b*) meet at a corner (180*e*). When a threaded portion (180*s*) of the mounting member is threadingly engaged with a mounting hole (300*h*) of a mount body (300), a forward-oriented surface (138*f*1) of the flange comes into contact with a mounting surface (300*r*) of the mount body, and the corner comes into contact with the slant surface.

8 Claims, 6 Drawing Sheets

GAS SENSOR AND GAS SENSOR INSTALLATION STRUCTURE

TECHNICAL FIELD

The present invention relates to a sensor having a sensor element, such as a gas sensor element for detecting a particular gas component, or a temperature sensor element, and to a sensor mounting structure.

BACKGROUND ART

Conventionally, a gas sensor is used for detecting the concentration of a particular component (oxygen, etc.) in exhaust gas from an internal combustion engine. The gas sensor has a gas sensor element therein. The gas sensor element is composed of a cell having a solid electrolyte member and a pair of electrodes disposed on the solid electrolyte member, etc. The gas sensor externally has a threaded portion and is mounted to a mount body (exhaust pipe, etc.) by means of the threaded portion being threadingly engaged with a mounting hole formed in the mount body.

Usually, after the gas sensor is mounted to an exhaust pipe, a connector connected to the lead wires extending from the gas sensor is connected to a connector of an external circuit or the like. However, in the case where the gas sensor and the external circuit are united without use of connectors or where the connector is to be fixed before the gas sensor is fixed, difficulty is encountered in threadingly engaging the gas sensor with the mounting hole, since the external circuit and the lead wires must be rotated together with the gas sensor.

In order to cope with such difficulty, there has been disclosed a technique in which a tubular rotary member is disposed in such a manner as to surround a metallic shell (housing) which holds a gas sensor element; is rotatable relative to the metallic shell; and has a threaded portion on its outer circumferential surface (refer to Patent Documents 1 and 2). By virtue of such a configuration, even when the gas sensor and the external circuit are united, the gas sensor can be threadingly engaged with the mounting hole without need to rotate the external circuit together therewith.

PRIOR ART DOCUMENTS

Patent Documents

[Patent Document 1] Japanese Patent Application Laid-Open (kokai) No. 2003-294685 (FIG. 2)
[Patent Document 2] PCT Application Laid-open No. 2006-514311

SUMMARY OF THE INVENTION

Problems to be Solved by the Invention

When the gas sensor is mounted to an automotive exhaust pipe or the like, the mounting location is exposed to a high temperature of 800° C. to 900° C. Thus, in a certain combination of a material of the mount body and a material of the rotary member, a screw clamp force may drop due to a difference in thermal expansion coefficient between the materials. In order to cope with the problem, the gas sensor described in Patent Document 1 has a specified screw tightening torque and has a gasket of a predetermined material disposed between the mounting surface of a mount body and the forward end surface of a housing.

However, the gas sensor described in Patent Document 1 involves the following problems: there is a limit on the combination of a material of the mount body and a material of the rotary member, and since the screw tightening torque must be strictly controlled, productivity and mounting workability of the gas sensor deteriorate.

In the case of the sensors described in Patent Documents 1 and 2, the housing has a flange projecting radially outward; the rotary member is disposed rearward of the flange; and when a threaded portion of the rotary member is threadingly engaged with a mounting hole of an exhaust pipe, the forward end surface (the surface on a side toward the exhaust pipe) of the rotary member is brought into contact with the surface of the flange, thereby fixing the housing to the mount body. However, in order for the rotary member to be rotatable relative to the housing, a clearance exists between the rotary member and the housing; therefore, the housing may be fixed while having an axial deviation relative to the mount body. In this case, the frictional force between the housing and the rotary member may lessen the screw tightening torque.

In view of the above problem, an object of the present invention is to provide a sensor which is threadingly engaged with a mounting hole of a mount body and is less likely to suffer slackness of screw engagement, without involvement of deterioration in productivity and mounting workability of the sensor, as well as a sensor mounting structure.

Means for Solving the Problems

In order to achieve the above object, the present invention provides a sensor extending in an axial direction and comprising a sensor element; a tubular metallic shell radially surrounding the sensor element; and a tubular mounting member radially surrounding the metallic shell, being rotatable relative to the metallic shell, and having, at its radially outer surface, a threaded portion to be threadingly engaged with a mounting hole of a mount body. The metallic shell has a body disposed radially inward of the mounting member, and a flange provided forward of the body and forward of the mounting member and projecting radially outward beyond a radially inner surface of the mounting member. As viewed on a section taken along the axial direction, a radially outer surface of the body of the metallic shell and a rearward-oriented surface of the flange of the metallic shell are connected by a slant surface formed such that the diameter of the slant surface increases toward the forward end thereof in the axial direction, and a forward-oriented surface of the mounting member and the radially inner surface of the mounting member meet at a corner. When the threaded portion of the mounting member is threadingly engaged with the mounting hole of the mount body, a forward-oriented surface of the flange of the metallic shell comes into contact with a mounting surface of the mount body, and the corner of the mounting member comes into contact with the slant surface of the metallic shell.

According to the sensor of the present invention, the forward-oriented surface of the flange of the metallic shell comes into contact with the mounting surface of the mount body, thereby providing a seal therebetween. Furthermore, when the corner of the mounting member comes into contact with the slant surface of the metallic shell, the slant surface applies stress to the corner and, in turn, to the mounting member in such a manner as to expand the mounting member radially outward. Thus, since the threaded portion at the radially outer surface of the mounting member also expands radially outward and is tightly engaged with a threaded portion of the mount body, even upon generation of vibration, the associated screw engagement is unlikely to slacken. Therefore, the sensor is less likely to suffer slackness of screw engagement without need to strictly control the screw tightening torque.

Also, since the corner of the mounting member is in contact with the slant surface of the metallic shell, the metallic shell does not have an axial deviation relative to the mount body. Therefore, there can be prevented the lessening of the screw tightening torque which could otherwise result from the frictional force between the metallic shell and the mounting member.

Notably, the "corner" is not limited to a corner where the forward-oriented surface and the radially inner surface of the mounting member meet at a right angle, but encompasses a corner where the forward-oriented surface and the radially inner surface meet at an acute angle or an obtuse angle. The "corner" further encompasses a chamfered corner and a radiused corner.

The "slant surface" is not limited to a taper surface which connects the radially outer surface of the body of the metallic shell and the rearward-oriented surface of the flange of the metallic shell, but encompasses a concave which is concaved frontward, and a convex which is convexed rearward.

Furthermore, in the sensor of the present invention, the slant surface of the metallic shell may be a taper surface formed such that the diameter of the taper surface gradually increases toward the forward end thereof in the axial direction. When the slant surface of the metallic shell assumes the form of such a taper surface, in screw tightening, stress increases uniformly, thereby facilitating a screw tightening operation.

Furthermore, in the sensor of the present invention, the mounting member has a body and a protrusion protruding axially forward from a forward end of the body and having a radial thickness thinner than that of the body, and the protrusion has the corner. Since, in the mounting member, the protrusion that is thinner in radial thickness than the body has the corner, when the corner comes into contact with the taper surface of the metallic shell, the protrusion becomes more likely to flex radially outward; accordingly, there increases stress applied in such a manner as to radially outwardly expand the protrusion and, in turn, the mounting member. Therefore, the threaded portion at the radially outer surface of the mounting member is engaged more firmly with the mount body, and the associated screw engagement becomes less likely to slacken.

The present invention also provides a sensor extending in an axial direction and comprising a sensor element; a tubular metallic shell radially surrounding the sensor element; and a tubular mounting member radially surrounding the metallic shell, being rotatable relative to the metallic shell, and having, at its radially outer surface, a threaded portion to be threadingly engaged with a mounting hole of a mount body. The metallic shell has a body disposed radially inward of the mounting member, and a flange provided forward of the body and forward of the mounting member and projecting radially outward beyond a radially inner surface of the mounting member. As viewed on a section taken along the axial direction, a rearward-oriented surface of the flange of the metallic shell and a radially outer surface of the flange meet at a corner, and a forward-oriented surface of the mounting member and the radially inner surface of the mounting member are connected by a slant surface formed such that the diameter of the taper surface increases toward the forward end thereof in the axial direction. When the threaded portion of the mounting member is threadingly engaged with the mounting hole of the mount body, a forward-oriented surface of the flange of the metallic shell comes into contact with a mounting surface of the mount body, and the corner of the flange of the metallic shell comes into contact with the slant surface of the mounting member.

According to the sensor of the present invention, the forward-oriented surface of the flange of the metallic shell comes into contact with the mounting surface of the mount body, thereby providing a seal therebetween. Furthermore, when the corner of the flange of the metallic shell comes into contact with the slant surface of the mounting member, the slant surface applies stress to the corner and, in turn, to the mounting member in such a manner as to expand the mounting member radially outward. Thus, since the threaded portion at the radially outer surface of the mounting member also expands radially outward and is tightly engaged with a threaded portion of the mount body, even upon generation of vibration, the associated screw engagement is unlikely to slacken. Therefore, the sensor is less likely to suffer slackness of screw engagement without need to strictly control the screw tightening torque.

Also, since the corner of the flange of the metallic shell is in contact with the slant surface of the mounting member, the metallic shell does not have an axial deviation relative to the mount body. Therefore, there can be prevented the lessening of the screw tightening torque which could otherwise result from the frictional force between the metallic shell and the mounting member.

Notably, the "corner" is not limited to a corner where the rearward-oriented surface and the radially outer surface of the flange of the metallic shell meet at a right angle, but encompasses a corner where the rearward-oriented surface and the radially outer surface meet at an acute angle or an obtuse angle. The "corner" further encompasses a chamfered or radiused corner where the rearward-oriented surface and the radially outer surface meet.

The "slant surface" is not limited to a taper surface which connects the forward-oriented surface and the radially inner surface of the mounting member, but encompasses a convex which is convexed forward, and a concave which is concaved rearward.

Furthermore, in the sensor of the present invention, the slant surface of the mounting member may be a taper surface formed such that the diameter of the taper surface gradually increases toward the forward end thereof in the axial direction. When the slant surface of the mounting member assumes the form of such a taper surface, in screw tightening, stress increases uniformly, thereby facilitating a screw tightening operation.

Furthermore, in the sensor of the present invention, the flange of the metallic shell has a first flange portion and a second flange portion disposed rearward of the first flange portion and having a radial thickness thinner than that of the first flange portion, and the second flange portion has the corner. Since the second flange portion that is thinner in radial thickness than the first flange portion has the corner, the slant surface of the mounting member can be brought into contact with the corner of the second flange portion of the flange of the metallic shell without involvement of reduction in the thickness of the mounting member. Therefore, deformation of the threaded portion of the mounting member can be prevented.

The present invention also provides a sensor mounting structure in which a sensor extending in the axial direction, comprising a sensor element, and having, at its radially outer surface, a threaded portion to be threadingly engaged with a mounting hole of a mount body, is threadingly engaged with the mounting hole of the mount body. The sensor mounting structure is characterized in that the sensor is the above-mentioned sensor of the present invention.

According to the sensor mounting structure of the present invention, the forward-oriented surface of the flange comes into contact with the mounting surface, thereby providing a seal therebetween. Furthermore, when the corner comes into contact with the slant surface, the slant surface applies stress to the corner and, in turn, to the mounting member in such a manner as to expand the mounting member radially outward. Thus, since the threaded portion at the radially outer surface of the mounting member also expands radially outward and is tightly engaged with a threaded portion of the mount body, even upon generation of vibration, the screw engagement of the threaded portions is unlikely to slacken.

Also, since the corner is in contact with the slant surface, the metallic shell does not have an axial deviation relative to the mount body. Therefore, there can be prevented the lessening of the screw tightening torque which could otherwise result from the frictional force between the metallic shell and the mounting member.

Effect of the Invention

According to the present invention, a sensor to be threadingly engaged with a mounting hole of a mount body can be less likely to suffer slackness of associated screw engagement without involvement of deterioration in productivity and mounting workability of the sensor.

MODES FOR CARRYING OUT THE INVENTION

Embodiments of the present invention will next be described with reference to the drawings.

Figure 1:
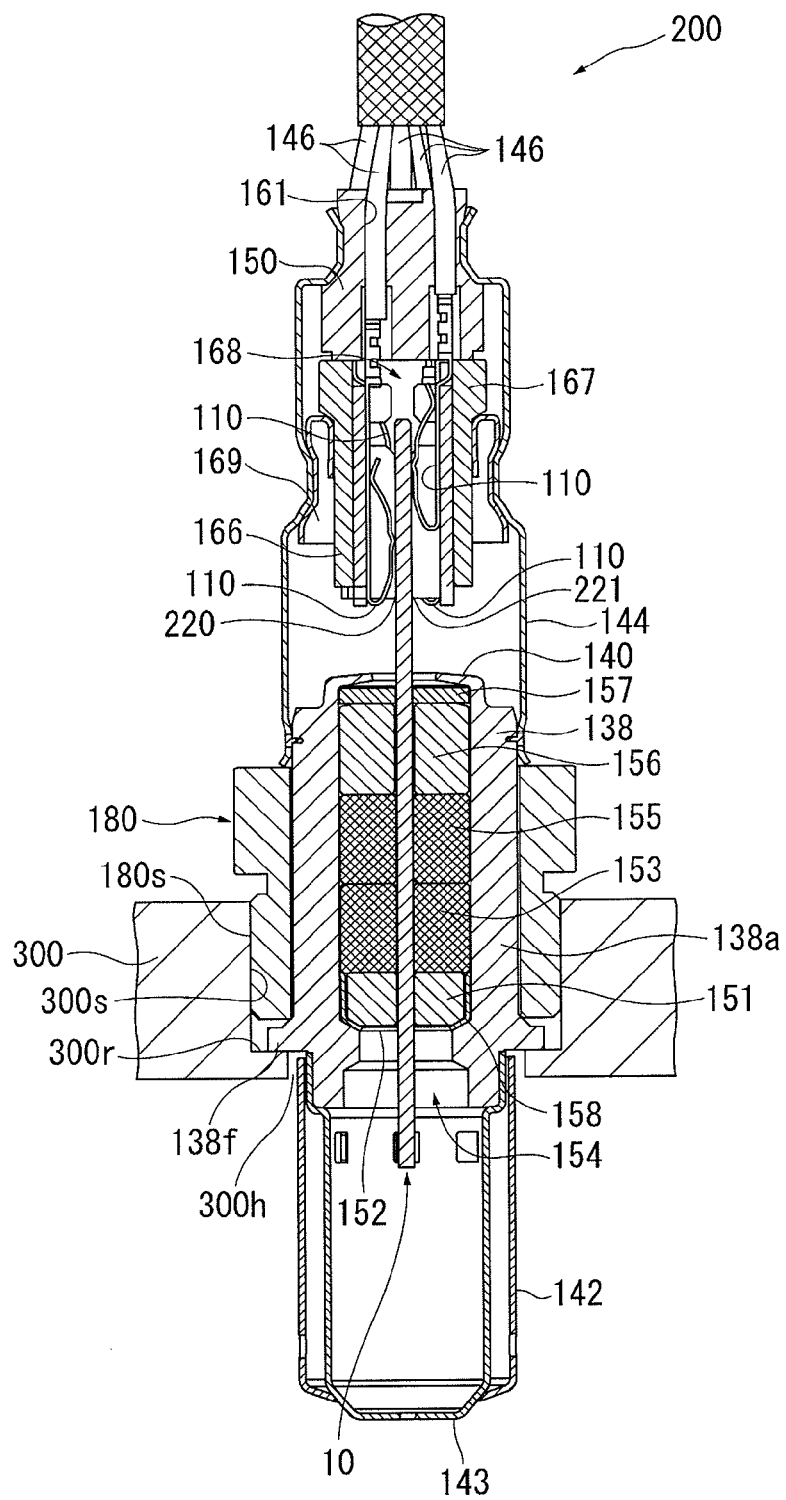
[FIG. 1] Sectional view of a gas sensor according to a first embodiment of the present invention taken along the longitudinal direction of the gas sensor.

FIG. 1 is a sectional view of a gas sensor ($NO_x$ sensor) 200 according to a first embodiment of the present invention taken along the longitudinal direction of the gas sensor 200, the gas sensor 200 including a gas sensor element ($NO_x$ sensor element) 10. The $NO_x$ sensor 200 includes the $NO_x$ sensor element (gas sensor element) 10 having a plate-like shape and extending in the axial direction (the longitudinal direction of the $NO_x$ sensor 200, or the vertical direction in FIG. 1); a tubular metallic shell (housing) 138; a mounting member 180 disposed radially around the metallic shell 138; an insulation contact member 166 disposed in such a manner that the wall surface of a contact insertion hole 168 extending therethrough in the axial direction radially surrounds a rear end portion of the $NO_x$ sensor element 10; and six connection terminals 110 (in FIG. 1; only four of them appear) disposed between the $NO_x$ sensor element 10 and the insulation contact member 166.

The metallic shell 138 assumes a substantially tubular shape and includes a body 138a which has a through hole 154 extending therethrough in the axial direction and a ledge 152 projecting radially inward in the through hole 154. The metallic shell 138 holds the $NO_x$ sensor element 10 in the through hole 154 in the following condition: a forward end portion of the $NO_x$ sensor element 10 is disposed externally of the forward end of the through hole 154, and electrode terminal portions 220 and 221 are disposed externally of the rear end of the through hole 154. Furthermore, the ledge 152 assumes the form of a radially inward taper surface inclined with respect to a plane perpendicular to the axial direction.

An annular ceramic holder 151, powder filler layers 153 and 155 (hereinafter, may be referred to as the talc rings 153 and 155), an annular ceramic sleeve 156, and a metal packing 157 are stacked in this order from the forward side to the rear side within the through hole 154 of the metallic shell 138 in such a manner as to radially surround the $NO_x$ sensor element 10. Also, a metal holder 158 is disposed between the ceramic holder 151 and the ledge 152 of the metallic shell 138 for holding the ceramic holder 151. A rear end portion 140 of the metallic shell 138 is crimped so as to press forward the metal packing 157.

Furthermore, the metallic shell 138 has a flange 138f located forward of the body 138a and projecting radially outward.

In the present embodiment, the $NO_x$ sensor element 10 is fixed by means of housing members of the gas sensor 200, such as the ceramic holder 151, and projects from the lower surface of the ceramic holder 151.

A mounting member 180 is disposed rearward of the flange 138f of the metallic shell 138 while radially surrounding the body 138a of the metallic shell 138, and is rotatable relative to the metallic shell 138. The mounting member 180 has, at its radially outer surface, a threaded portion (external thread) 180s to be threadingly engaged with a mounting hole 300h of a mount body 300.

The mount body 300 is, for example, an automotive exhaust pipe and has a threaded portion (internal thread) 300s formed at a wall surface of the mounting hole 300h located on an axially outer side, and the threaded portion 300s is engaged with the threaded portion 180s. Also, the mount body 300 has a seat projecting radially inward from a wall surface of the mounting hole 300h located on an axially inner side, and the seat has a mounting surface 300r to come into contact with a forward-oriented surface 138f1 (see FIG. 3) of the flange 138f.

Meanwhile, as shown in FIG. 1, a dual-structure protector which covers a projecting portion of the $NO_x$ sensor element 10 and which consists of an outer protector 142 and an inner protector 143 made of metal (e.g., stainless steel) and having a plurality of holes is attached, by welding or the like, to the outer circumference of a forward end portion (in FIG. 1, a lower end portion) of the metallic shell 138.

A tubular sheath 144 is fixed to the outer circumference of a rear end portion of the metallic shell 138. A grommet 150 is disposed in a rear-end (in FIG. 1, an upper-end) opening portion of the tubular sheath 144. The grommet 150 has lead-wire insertion holes 161 through which six lead wires 146 (in FIG. 1, only five lead wires appear) are inserted respectively for electrical connection to the electrode terminal portions 220 and 221 of the $NO_x$ sensor element 10.

The insulation contact member 166 is disposed at a position corresponding to a rear end portion (in FIG. 1, an upper end portion) of the $NO_x$ sensor element 10 which projects from the rear end portion 140 of the metallic shell 138. The insulation contact member 166 is disposed around the electrode terminal portions 220 and 221 formed on the surface of the rear end portion of the $NO_x$ sensor element 10. The insulation contact member 166 assumes a tubular shape and has the contact insertion hole 168 extending therethrough in the axial direction, as well as a flange portion 167 projecting radially outward from the radially outer surface thereof. The insulation contact member 166 is disposed within the tubular sheath 144 by means of the flange portion 167 coming in contact with the tubular sheath 144 via a holding member 169.

Next, the structure of the $NO_x$ sensor element 10 will be described with reference to FIG. 2, which is a sectional view taken along the longitudinal direction. The "longitudinal direction" is of the NO sensor element 10 and is perpendicular to the stacking direction of the layers of the NO sensor element 10.

Figure 2:
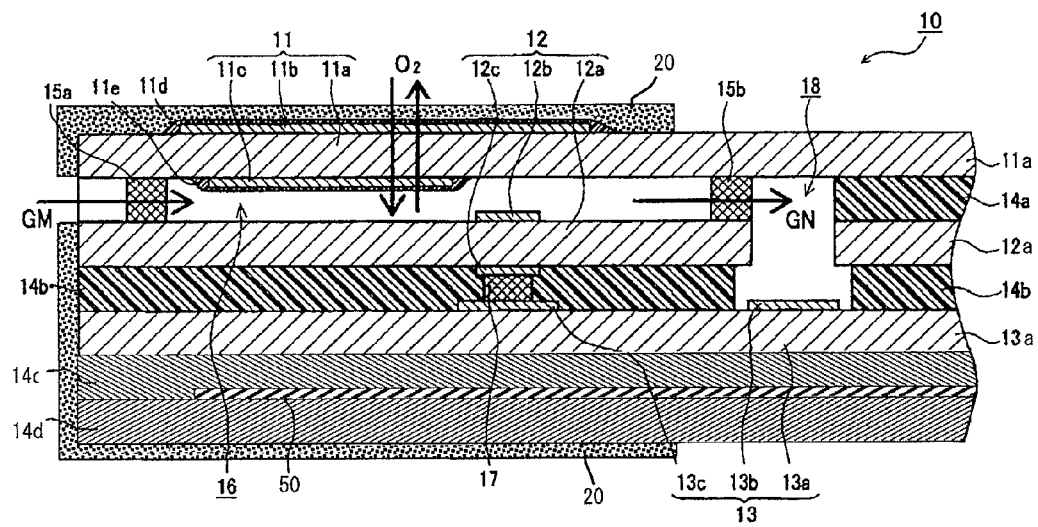
[FIG. 2] Sectional view of an $NO_x$ sensor element taken along the longitudinal direction of the $NO_x$ sensor element.

In FIG. 2, the NO sensor element 10 has a structure in which a first solid electrolyte layer 11a, an insulation layer 14a, a second solid electrolyte layer 12a, an insulation layer 14b, a third solid electrolyte layer 13a, and insulation layers 14c and 14d are laminated together in this order. A first measuring chamber 16 is formed between the first solid electrolyte layer 11a and the second solid electrolyte layer 12a. A gas-to-be-measured GM is externally introduced into the first measuring chamber 16 via a first diffusion resistor 15a disposed at the left end (inlet) of the first measuring chamber 16.

A second diffusion resistor 15b is disposed at an end of the first measuring chamber 16 opposite the inlet. A second measuring chamber 18 is formed at the right of the first measuring chamber 16 and communicates with the first measuring chamber 16 via the second diffusion resistor 15b. The second measuring chamber 18 extends through the second solid electrolyte layer 12a and is formed between the first solid electrolyte layer 11a and the third solid electrolyte layer 13a.

An elongated plate-like heater 50 is embedded between the insulation layers 14c and 14d and extends along the longitudinal direction of the NO sensor element 10. The heater 50 heats the $NO_x$ sensor element 10 to a predetermined activation temperature for stabilizing operation through enhancement of oxygen ion conductivity of the solid electrolyte layers.

The insulation layers 14a to 14d are formed by using alumina as a main component. The first diffusion resistor 15a and the second diffusion resistor 15b are formed from a porous material of alumina or the like. The heater 50 is formed from platinum or the like.

A first pumping cell 11 includes the first solid electrolyte layer 11a, an inner first pump electrode 11c, and a first counter electrode (outer first pump electrode) 11b, which is a counter electrode of the inner first pump electrode 11c. The first solid electrolyte layer 11a predominantly contains zirconia, which has oxygen ion conductivity. The inner first pump electrode 11c and the outer first pump electrode 11b are disposed in such a manner that the first solid electrolyte layer 11a is sandwiched therebetween. The inner first pump electrode 11c faces the first measuring chamber 16. The inner first pump electrode 11c and the outer first pump electrode 11b predominantly contain platinum. The surfaces of the inner first pump electrode 11c and the outer first pump electrode 11b are covered with protection layers 11e and 11d, respectively, formed from a porous material.

An oxygen concentration detection cell 12 includes the second solid electrolyte layer 12a, a detection electrode 12b, and a reference electrode 12c. The second solid electrolyte layer 12a predominantly contains zirconia. The detection electrode 12b and the reference electrode 12c are disposed in such a manner that the second solid electrolyte layer 12a is sandwiched therebetween. The detection electrode 12b is located downstream of the inner first pump electrode 11c and faces the first measuring chamber 16. The detection electrode 12b and the reference electrode 12c predominantly contain platinum.

The insulation layer 14b has a cutout formed in such manner as to accommodate the reference electrode 12c in contact with the second solid electrolyte layer 12a. The cutout is filled with a porous material, thereby forming a reference oxygen chamber 17. Application of extremely weak constant current to the oxygen concentration detection cell 12 causes oxygen to be sent into the reference oxygen chamber 17 from the first measuring chamber 16, thereby establishing a reference oxygen concentration.

A second pumping cell 13 includes the third solid electrolyte layer 13a, an inner second pump electrode 13b, and a second counter electrode (counter second pump electrode) 13c. The third solid electrolyte layer 13a predominantly contains zirconia. The inner second pump electrode 13b is disposed on a surface of the third solid electrolyte layer 13a which faces the second measuring chamber 18. The second counter electrode 13c is a counter electrode of the inner second pump electrode 13b. The inner second pump electrode 13b and the counter second pump electrode 13c predominantly contain platinum.

The counter second pump electrode 13c is disposed on the third solid electrolyte layer 13a and in a cutout of the insulation layer 14b, and faces the reference electrode 12c with the reference oxygen chamber 17 therebetween.

The $NO_x$ sensor element 10 has a porous protection layer 20 which covers the outer first pump electrode 11b.

Figure 3:
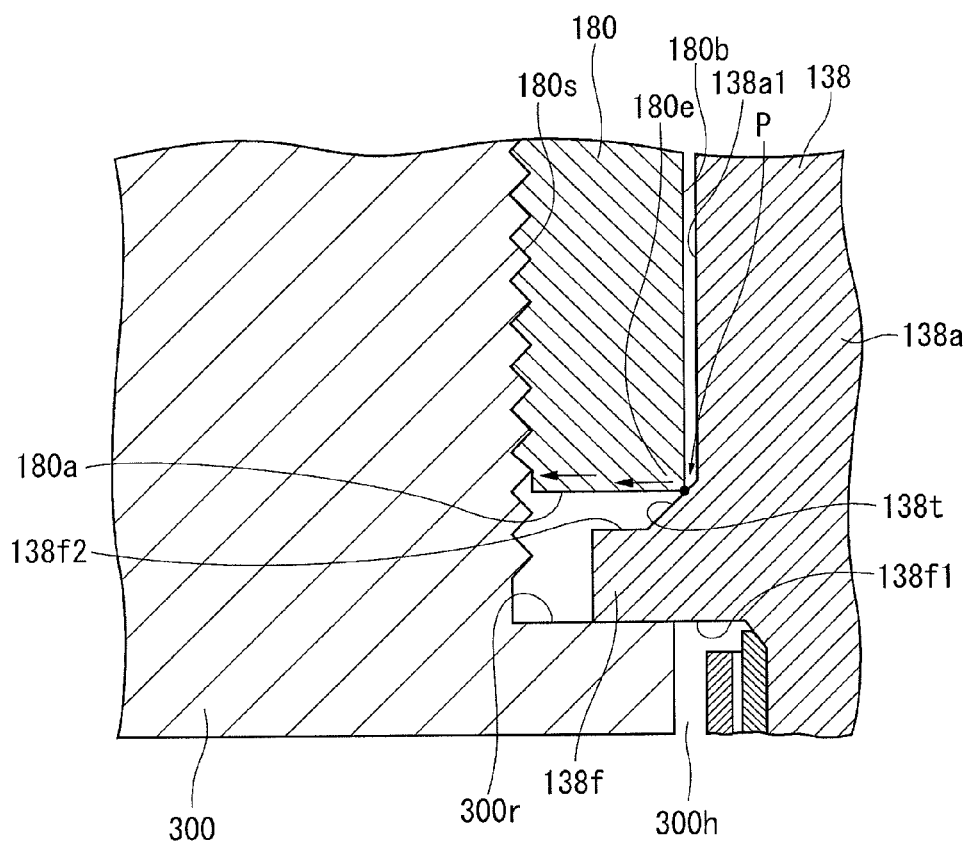
[FIG. 3] Enlarged fragmentary view of FIG. 1, showing how the flange of a metallic shell and a mounting member are in contact with each other.

Next, how the metallic shell 138 and the mounting member 180 are in contact with each other will be described with reference to FIG. 3. FIG. 3 is an enlarged fragmentary view of FIG. 1. FIG. 3 corresponds to "a section taken along the axial direction" appearing in claims.

In FIG. 3, the metallic shell 138 is such that a rearward-oriented surface 138f2 of the flange 138f and a radially outer surface 138a1 of the body 138a are connected by a taper surface 138t (which corresponds to "a slant surface" appearing in claims) formed such that the diameter of the taper surface increases toward the forward end thereof in the axial direction. Meanwhile, the mounting member 180 is such that a forward-oriented surface 180a and a radially inner surface 180b meet at a corner 180e having an angle of 90 degrees.

Thus, when the threaded portion 180s of the mounting member 180 is threadingly engaged with the mounting hole 300h of the mount body 300, the forward-oriented surface 138f1 of the flange 138f comes into contact with the mounting surface 300r of the mount body 300, thereby providing a seal therebetween. Furthermore, the corner 180e is in contact with the taper surface 138t at a contact point P. At this time, the taper surface 138t applies stress to the corner 180e and, in turn, to the mounting member 180 in such a manner as to expand the mounting member 180 radially outward. Thus, since the threaded portion 180s at the radially outer surface of the mounting member 180 also expands radially outward and is tightly engaged with the threaded portion 300s of the mount body 300, even upon generation of vibration, the screw engagement of the threaded portions 180s and 300s is unlikely to slacken. Also, since slackness is mechanically prevented by expanding the threaded portion 180s radially outward, there is no need to particularly consider the difference in thermal expansion coefficient between a material of the metallic shell 138 and a material used to form a boss aperture; therefore, no particular limitation is imposed on materials of component members of the gas sensor 200.

Also, since the corner 180e is in contact with the taper surface 138t at the contact point P, the metallic shell 138 does not have an axial deviation relative to the mount body 300. Therefore, there can be prevented the lessening of the tightening torque of the threaded portion 180s which could otherwise result from the frictional force between the metallic shell 138 and the mounting member 180.

Next, an example operation of the $NO_x$ sensor element 10 is described. When an engine gets started, and the gas sensor 200 receives power from an external power supply, the heater 50 is activated via a predetermined control circuit and heats the first pumping cell 11, the oxygen concentration detection cell 12, and the second pumping cell 13 to an activation temperature. When the cells 11 to 13 are heated to the activation temperature, the first pumping cell 11 pumps out excess oxygen contained in the gas-to-be-measured GM (exhaust gas) which has been introduced into the first measuring chamber 16, from the inner first pump electrode 11c toward the first counter electrode 11b. At this time, a first pump current Ip1 flows to the first pumping cell 11.

Since the oxygen concentration in the first measuring chamber 16 corresponds to the electrode-to-electrode voltage (terminal-to-terminal voltage) Vs of the oxygen concentration detection cell 12, the electrode-to-electrode voltage (terminal-to-terminal voltage) Vp1 of the first pumping cell 11 is controlled so that the electrode-to-electrode voltage Vs becomes a fixed voltage V1 (e.g., 425 mV), thereby adjusting the oxygen concentration of the first measuring chamber 16 to such a level as not to cause decomposition of $NO_x$.

The gas-to-be-measured GN whose oxygen concentration has been adjusted flows toward the second measuring chamber 18. Such a fixed electrode-to-electrode voltage (terminal-to-terminal voltage) Vp2 as to cause decomposition of $NO_x$ contained in the gas-to-be-measured GN into oxygen and nitrogen (a voltage higher than the control voltage of the oxygen concentration detection cell 12; e.g., 450 mV) is applied to the second pumping cell 13, thereby decomposing $NO_x$ into nitrogen and oxygen. A second pump current Ip2 flows to the second pumping cell 13 so as to pump out oxygen generated through decomposition of $NO_x$ from the second measuring chamber 18. Since there is a linear relationship between the second pump current Ip2 and the $NO_x$ concentration, through detection of the current Ip2, the $NO_x$ concentration in the gas-to-be-measured GN can be detected.

Next, a gas sensor according to a second embodiment of the present invention will be described with reference to FIG. 4. The gas sensor according to the second embodiment is similar to the gas sensor according to the first embodiment, except for the structure of a forward end of the mounting member 180. By use of FIG. 4, which is an enlarged fragmentary view corresponding to FIG. 3, configurational features different from those of the first embodiment will be described.

Figure 4:
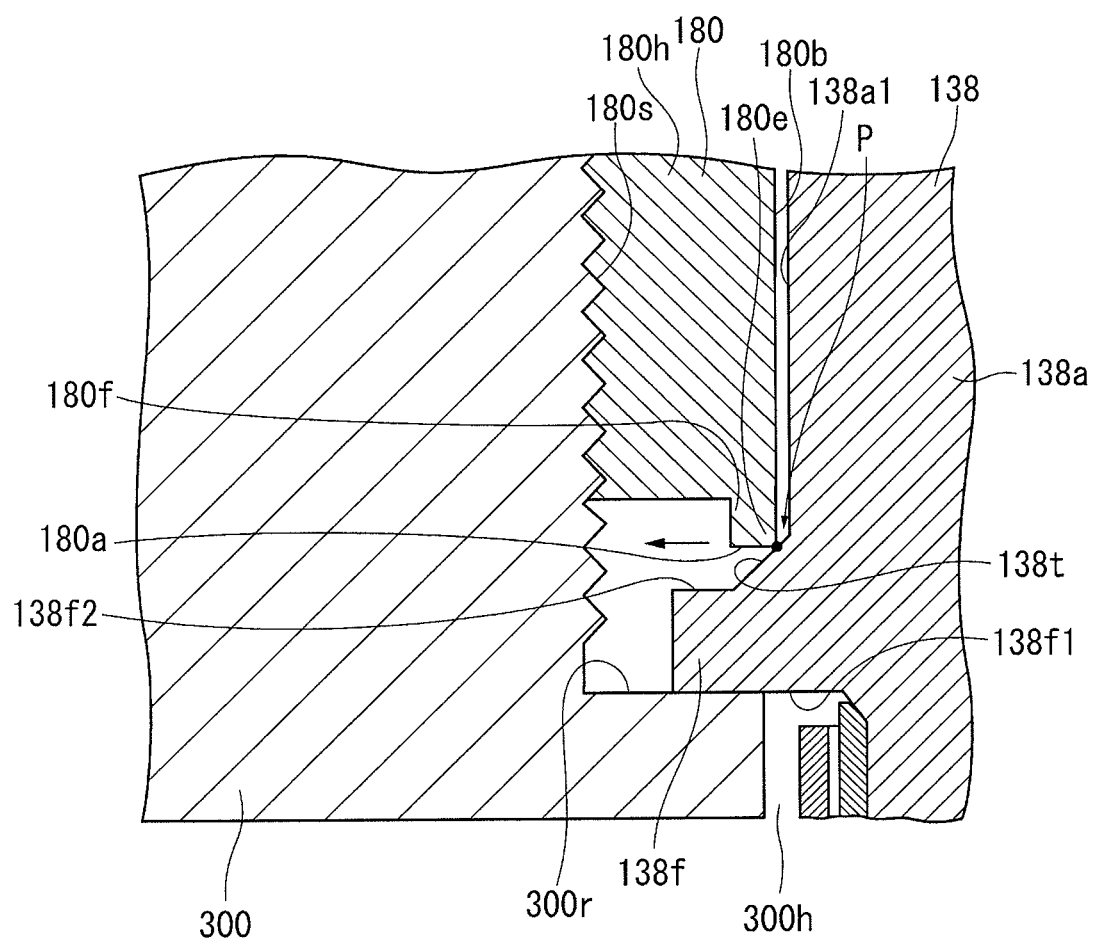
[FIG. 4] Enlarged fragmentary sectional view showing a gas sensor according to a second embodiment of the present invention.

In FIG. 4, the mounting member 180 has a body 180h and a protrusion 180f protruding axially forward from the forward end of the body 180h and having a radial thickness thinner than that of the body 180h. The protrusion 180f is such that the forward-oriented surface 180a and the radially inner surface 180b meet at the corner 180e having an angle of 90 degrees.

Thus, when the threaded portion 180s of the mounting member 180 is threadingly engaged with the mounting hole 300h of the mount body 300, the corner 180e comes into contact with the taper surface 138t. At this time, since the protrusion 180f having a thinner radial thickness is more likely to flex radially outward, stress associated with the protrusion 180f and, in turn, the mounting member 180 attempting to expand radially outward further increases. Accordingly, the threaded portion 180s is more tightly engaged with the threaded portion 300s, and associated screw engagement is more unlikely to slacken.

Next, a gas sensor according to a third embodiment of the present invention will be described with reference to FIG. 5. The gas sensor according to the third embodiment is similar to the gas sensor according to the first embodiment except that the mounting member 180 has a taper surface, and the flange 138f has a corner. By use of FIG. 5, which is an enlarged fragmentary view corresponding to FIG. 3, configurational features different from those of the first embodiment will be described.

Figure 5:
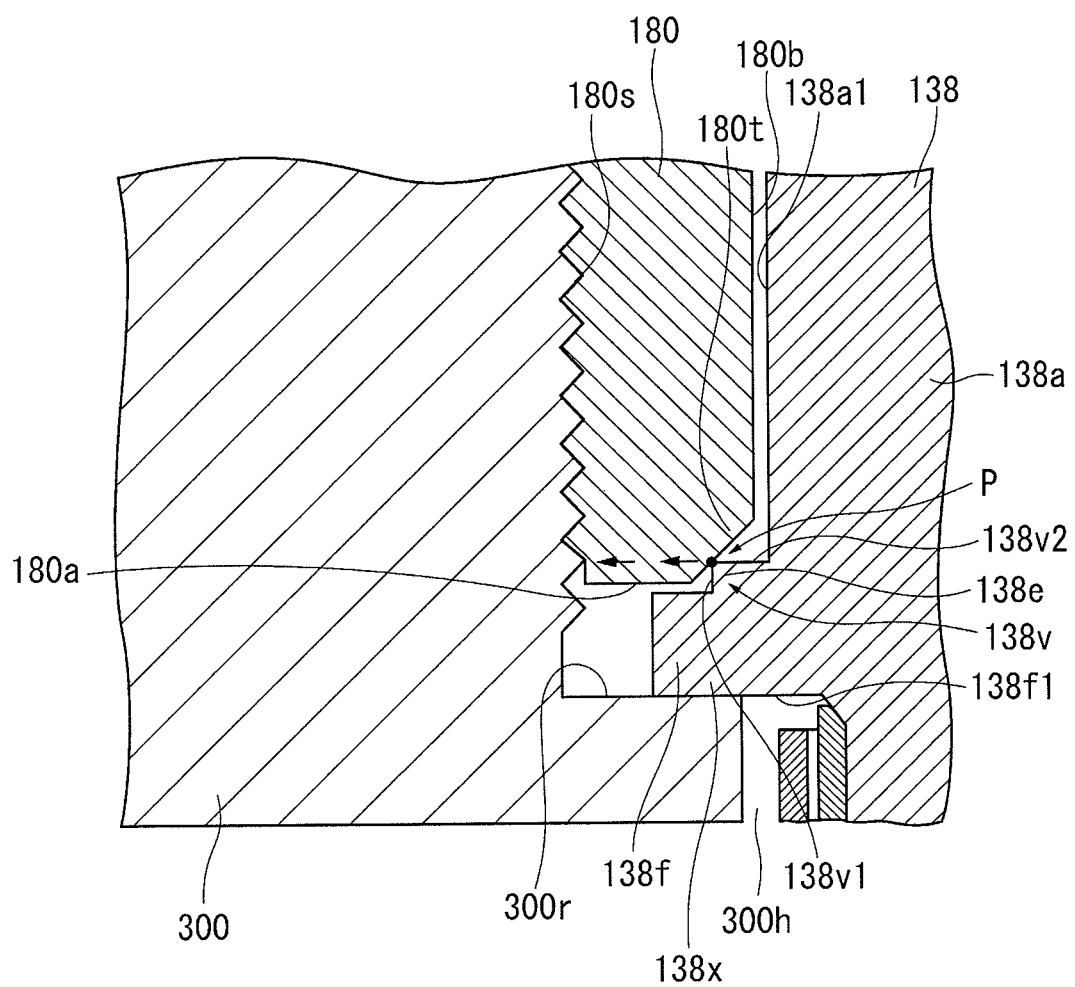
[FIG. 5] Enlarged fragmentary sectional view showing a gas sensor according to a third embodiment of the present invention.

In FIG. 5, the flange 138f has a first flange portion 138x and a second flange portion 138v disposed rearward of the first flange portion 138x and having a radial thickness thinner than that of the first flange portion 138x. A rearward-oriented surface 138v2 of the second flange portion 138v and a radially outer surface 138v1 of the second flange portion 138v meet at a corner 138e having an angle of 90 degrees. Meanwhile, the mounting member 180 is such that the forward-oriented surface 180a and the radially inner surface 180b are connected by a taper surface 180t (corresponding to an "slant surface" appearing in claims) formed such that the diameter of the taper surface increases toward the forward end thereof in the axial direction.

Thus, when the threaded portion 180s of the mounting member 180 is threadingly engaged with the mounting hole 300h of the mount body 300, as in the case of the first embodiment, the corner 138e comes into contact with the taper surface 180t at the contact point P. At this time, the taper surface 180t applies stress to the mounting member 180 in such a manner as to expand the mounting member 180 radially outward. Therefore, since the threaded portion 180s at the radially outer surface of the mounting member 180 also expands radially outward and is tightly engaged with the threaded portion 300s of the mount body 300, even upon generation of vibration, the associated screw engagement is unlikely to slacken.

Also, since the corner 138e is in contact with the taper surface 180t, the metallic shell 138 does not have an axial deviation relative to the mount body 300. Therefore, there can be prevented the lessening of the screw tightening torque of the threaded portion 180s which could otherwise result from the frictional force between the metallic shell 138 and the mounting member 180.

Furthermore, the second flange portion 138v that is thinner in radial thickness than the first flange portion 138x has the corner 138e. In this manner, by means of the second flange portion 138v thinner in radial thickness than the first flange portion 138x having the corner 138e, the taper surface 180t can be brought into contact with the corner 138e without involvement of reduction in the thickness of the mounting member 180. Therefore, deformation of the threaded portion 180s of the mounting member 180 can be prevented.

The present invention is not limited to the above embodiments, but may encompass various modifications and equivalents thereof without departing from the gist of the invention.

For example, in the gas sensors according to the first to third embodiments, the corners 138e and 180e have an angle of 90 degrees. However, the present invention is not limited thereto. The corners may have an acute or obtuse angle. Furthermore, the corners may be chamfered or radiused.

Also, in the gas sensor according to the third embodiment, the flange 138f has the first flange portion 138x and the second flange portion 138v. However, the present invention is not limited thereto. The entire flange may have the uniform radial thickness.

Furthermore, examples of the gas sensor element include, in addition to the above-described $NO_x$ sensor element, an oxygen sensor (λ sensor) element, a full-range air/fuel ratio sensor element, and an ammonia sensor element. Examples of a sensor element other than the gas sensor element include a temperature sensor element. The present invention can be used in a temperature sensor, etc., in addition to a gas sensor.

Figure 6:
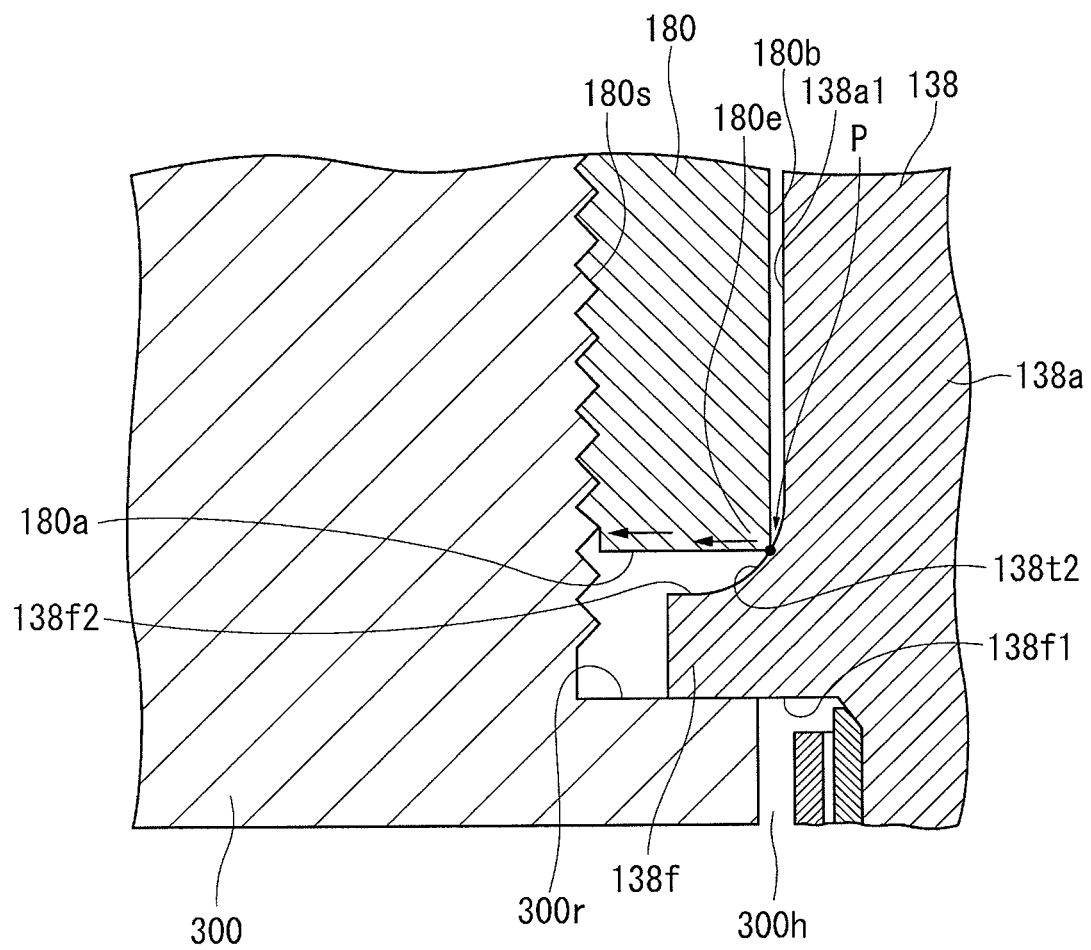
[FIG. 6] View showing the case where a concave surface is provided in place of the taper surface shown in FIG. 3.

Also, as shown in FIG. 6, in place of the taper surface 138*t* shown in FIG. 3, a concave surface (a radiused surface) 138*t*2 may be provided as a slant surface. Similarly, as shown in FIG. 7, in place of the taper surface 180*t* shown in FIG. 5, a convex surface (a radiused surface) 180*t*2 may be provided as a slant surface.

Figure 7:
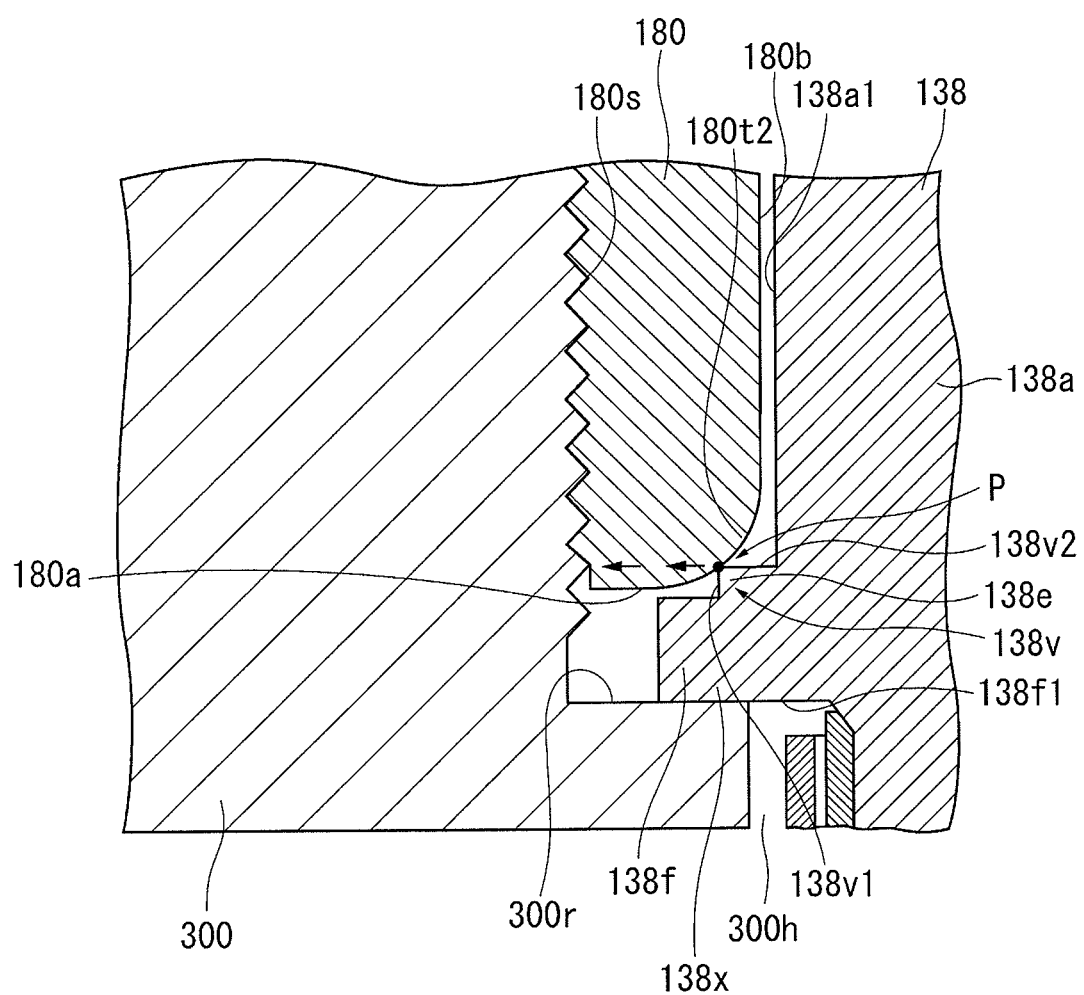
[FIG. 7] View showing the case where a convex surface is provided in place of the taper surface shown in FIG. 5.

Furthermore, in FIG. 6, the concave surface is provided as a slant surface; however, in FIG. 6, a convex surface like the convex surface 180*t*2 shown in FIG. 7 may be provided in place of the concave surface. Similarly, in FIG. 7, the convex surface is provided as a slant surface; however, in FIG. 7, a concave surface like the concave surface 138*t*2 shown in FIG. 6 may be provided in place of the convex surface.

DESCRIPTION OF REFERENCE NUMERALS

10: sensor element ($NO_x$ sensor element)
138: metallic shell
138*a*: body of metallic shell
138*e*: corner of flange
138*f*: flange
138*f*1: forward-oriented surface of flange
138*t*, 138*t*2: slant surface of flange
138*x*: first flange portion
138*v*: second flange portion
180: mounting member
180*a*: forward-oriented surface of mounting member
180*b*: radially inner surface of mounting member
180*e*: corner of mounting member
180*f*: protrusion of mounting member
180*h*: body of mounting member
180*s*: threaded portion of mounting member
180*t*, 180*t*2: slant surface of mounting member
200: sensor
300: mount body
300*h*: mounting hole
300*r*: mounting surface

The invention claimed is:

1. A sensor extending in an axial direction and comprising:
a sensor element;
a tubular metallic shell radially surrounding the sensor element; and
a tubular mounting member radially surrounding the metallic shell, being rotatable relative to the metallic shell, and having, at its radially outer surface, a threaded portion to be threadingly engaged with a mounting hole of a mount body;
wherein the metallic shell has a body disposed radially inward of the mounting member, and a flange provided forward of the body and forward of the mounting member and projecting radially outward beyond a radially inner surface of the mounting member;
as viewed on a section taken along the axial direction, a radially outer surface of the body of the metallic shell and a rearward-oriented surface of the flange of the metallic shell are connected by a slant surface formed such that the diameter of the slant surface increases toward the forward end thereof in the axial direction, and a forward-oriented surface of the mounting member and the radially inner surface of the mounting member meet at a corner; and
when the threaded portion of the mounting member is threadingly engaged with the mounting hole of the mount body, a forward-oriented surface of the flange of the metallic shell comes into contact with a mounting surface of the mount body, and the corner of the mounting member comes into contact with the slant surface of the metallic shell.

2. A sensor mounting structure in which a sensor extending in the axial direction, comprising a sensor element, and having, at its radially outer surface, a threaded portion to be threadingly engaged with a mounting hole of a mount body, is threadingly engaged with the mounting hole of the mount body,
characterized in that the sensor is the one as claimed in claim 1.

3. A sensor as claimed in claim 1, wherein the slant surface of the metallic shell is a taper surface formed such that the diameter of the taper surface gradually increases toward the forward end thereof in the axial direction.

4. A sensor as claimed in claim 1, wherein the mounting member has a body and a protrusion protruding axially forward from a forward end of the body and having a radial thickness smaller than that of the body, and the protrusion has the corner.

5. A sensor extending in an axial direction and comprising:
a sensor element;
a tubular metallic shell radially surrounding the sensor element; and
a tubular mounting member radially surrounding the metallic shell, being rotatable relative to the metallic shell, and having, at its radially outer surface, a threaded portion to be threadingly engaged with a mounting hole of a mount body;
wherein the metallic shell has a body disposed radially inward of the mounting member, and a flange provided forward of the body and forward of the mounting member and projecting radially outward beyond a radially inner surface of the mounting member;
as viewed on a section taken along the axial direction, a rearward-oriented surface of the flange of the metallic shell and a radially outer surface of the flange meet at a corner, and a forward-oriented surface of the mounting member and the radially inner surface of the mounting member are connected by a slant surface formed such that the diameter of the slant surface increases toward the forward end thereof in the axial direction; and
when the threaded portion of the mounting member is threadingly engaged with the mounting hole of the mount body, a forward-oriented surface of the flange of the metallic shell comes into contact with a mounting surface of the mount body, and the corner of the flange of the metallic shell comes into contact with the slant surface of the mounting member.

6. A sensor as claimed in claim 5, wherein the slant surface of the mounting member is a taper surface formed such that the diameter of the taper surface gradually increases toward the forward end thereof in the axial direction.

7. A sensor as claimed in claim 5, wherein the flange of the metallic shell has a first flange portion and a second flange portion disposed rearward of the first flange portion and having a radial thickness thinner than that of the first flange portion, and the second flange portion has the corner.

8. A sensor mounting structure in which a sensor extending in the axial direction, comprising a sensor element, and having, at its radially outer surface, a threaded portion to be threadingly engaged with a mounting hole of a mount body, is threadingly engaged with the mounting hole of the mount body,
characterized in that the sensor is the one as claimed in claim 5.

* * * * *